United States Patent [19]
Bocek et al.

[11] Patent Number: 5,578,063
[45] Date of Patent: Nov. 26, 1996

[54] IMPLANTABLE ATRIAL DEFIBRILLATOR AND SYSTEM HAVING MULTIPLE CHANNEL ELECTROGRAM TELEMETRY AND METHOD

[75] Inventors: Joseph M. Bocek, Seattle; Craig S. Siegman, Redmond, both of Wash.

[73] Assignee: InControl, Inc., Redmond, Wash.

[21] Appl. No.: 545,397

[22] Filed: Oct. 19, 1995

[51] Int. Cl.$^6$ .................................................. A61N 1/39
[52] U.S. Cl. ................................................................ 607/5
[58] Field of Search ........................................ 607/5, 4, 7

[56] References Cited

U.S. PATENT DOCUMENTS

| | | | |
|---|---|---|---|
| 5,203,326 | 4/1993 | Collins | 607/4 |
| 5,300,093 | 4/1994 | Koestner et al. | 607/32 |
| 5,441,519 | 8/1995 | Sears | 607/5 |
| 5,507,780 | 4/1996 | Finch | 607/5 |

FOREIGN PATENT DOCUMENTS

| | | | |
|---|---|---|---|
| 9218198 | 10/1992 | WIPO | 607/5 |

Primary Examiner—George Manuel
Assistant Examiner—Carl H. Layno
Attorney, Agent, or Firm—Richard O. Gray, Jr.

[57] ABSTRACT

A defibrillator system includes an implantable defibrillator and a non-implantable external receiver. The implantable defibrillator includes a first sense channel for generating a first electrogram and a second sense channel for generating a second electrogram. The defibrillator further includes a cardioverter for applying cardioverting electrical energy to the heart and a transmitter for transmitting the first and second electrograms. The non-implantable receiver includes a display for simultaneously displaying the first and second electrograms. The implantable defibrillator may further include an event detector having a threshold for detecting cardiac events in one of the electrograms and an event marker generator for generating an event marker for each detected cardiac event. The transmitter transmits the event detection markers and the display displays the event detection markers and the thresholds with the corresponding electrogram.

26 Claims, 6 Drawing Sheets

IMPLANTABLE ATRIAL DEFIBRILLATOR AND SYSTEM HAVING MULTIPLE CHANNEL ELECTROGRAM TELEMETRY AND METHOD

BACKGROUND OF THE INVENTION

The present invention generally relates to an automatic implantable atrial defibrillator, system, and method for delivering cardioverting or defibrillating electrical energy to the atria of a human heart and which is capable of providing the cardiologist with important information related to the condition of the patient and the interaction between the implanted defibrillator and the patient's heart. More particularly, the atrial defibrillator of the present invention is capable of transmitting, for simultaneous display on an external programer display, multiple internally generated electrograms, one or more internally generated electrograms with event detection criteria and/or event detection indicia, or multiple internally generated electrograms together with indicia showing when cardioverting energy delivery criteria are satisfied by the patient's heart activity.

Atrial fibrillation is probably the most common cardiac arrhythmia. Although it is not usually a life threatening arrhythmia, it is associated with strokes thought to be caused by blood clots forming in areas of stagnant blood flow as a result of prolonged atrial fibrillation. Patients afflicted with atrial fibrillation generally experience palpitations of the heart and may even experience dizziness or even loss of consciousness.

Atrial fibrillation occurs suddenly and many times can only be corrected by external defibrillation of the type well known in the art. This treatment involves applying a relatively large quantity of electrical energy to the heart with external skin surface electrodes. The energy is applied in synchronism with a detected R wave (electrical activation) of the heart. The treatment is very painful and can necessitate hospitalization for as many as a few days. Unfortunately, most often, it only provides temporary relief, lasting but a few weeks.

Drugs are available for reducing the incidents of atrial fibrillation. However, such drugs have many side effects. Also, many patients are resistant to them which greatly reduces their therapeutic effect.

In order to negate the need for external defibrillation and drug therapy, implantable atrial defibrillators have been proposed to provide relief for patients suffering from occurrences of atrial fibrillation. Two such defibrillators, although represented as being implantable, were not fully automatic, requiring human interaction for cardioverting or defibrillating the heart. Both of these defibrillators required the patient to recognize the symptoms of atrial fibrillation. One defibrillator required a visit to a physician for activating the defibrillator. The other defibrillator required the patient to activate the defibrillator with a magnet from external to the patient's skin.

It is preferable that an implantable cardiac device, such as an atrial defibrillator, be truly automatic. In order for an implantable atrial defibrillator to be truly automatic, it must be able to accurately detect atrial fibrillation and then safely apply electrical energy to the atria to convert the same to normal sinus rhythm (NSR).

Detection of atrial fibrillation is a two-part process. First, an atrial defibrillator must be able to sense activity of the heart, such as atrial activity. One atrial defibrillator having such capability is fully disclosed in Jin et al., U.S. Pat. No. 5,267,559 which issued on Dec. 7, 1993 for ATRIAL DEFIBRILLATOR AND METHOD FOR PROVIDING ATRIAL SENSING and which is assigned to the assignee of the present invention and incorporated herein by reference.

After heart activity, such as atrial activity, is sensed, an atrial fibrillation detector then must determine if the sensed heart activity satisfies a fibrillation criteria. One such detector is fully disclosed in co-pending U.S. application Ser. No. 08/233,251, now U.S. Pat. No. 5,522,852, filed Apr. 26, 1994 in the names of Harley G. White and Joseph M. Bocek for SELECTIVE CARDIAC ACTIVITY ANALYSIS ATRIAL FIBRILLATION DETECTION SYSTEM AND METHOD AND ATRIAL DEFIBRILLATOR UTILIZING SAME. Another such detector is fully disclosed in co-pending U.S. application Ser. No. 08/278,055, now U.S. Pat. No. 5,486,199, filed Jul. 20, 1994 in the names of Jaeho Kim and Harley G. White for SYSTEM AND METHOD FOR REDUCING FALSE POSITIVES IN ATRIAL FIBRILLATION DETECTION. Both of the aforementioned co-pending applications are assigned to the assignee of the present invention and incorporated herein by reference.

Each of the aforementioned co-pending applications discloses a preferred embodiment of an atrial fibrillation detector wherein atrial cardiac events are detected from sensed atrial activity. Further, each of these preferred embodiments includes ventricular activity sensing and the detection of R waves from the sensed ventricular activity.

Once atrial fibrillation is detected, it is then preferred to apply cardioverting electrical energy to the atria to return the heart to NSR. To assure that the cardioverting electrical energy is safely applied to the atria, it is preferred that the energy be applied in synchronism with a detected R wave. To that end, co-pending U.S. application Ser. No. 08/259,476 filed Jun. 14, 1994 in the name of Harley G. White for CARDIOVERSION SYNCHRONIZATION SYSTEM AND METHOD FOR AN ATRIAL DEFIBRILLATOR, which is assigned to the assignee of the present invention and incorporated herein by reference discloses a synchronization system which includes two ventricular sense channels and requires that an R wave be sensed in both channels before the energy may be applied. In addition, other synchronization criteria may be required to be satisfied such as a minimum interval criteria as described, for example, in Adams, et al., U.S. Pat. No. 5,207,219, which issued on May 4, 1993 for ATRIAL DEFIBRILLATOR AND METHOD FOR PROVIDING INTERVAL TIMING PRIOR TO CARDIOVERSION, and which is assigned to the assignee of the present invention and incorporated herein by reference.

Hence, as can be seen from the foregoing, an automatic atrial defibrillator must reliably sense heart activity, reliably detect cardiac events, and apply energy delivery criteria to sensed heart activity. In order to assure that the defibrillator will perform the above functions at the time of implant and thereafter, it would be desirable for the defibrillator to have the capability to provide the cardiologist with adequate information to verify that it is functioning appropriately. For example, in addition to cardiac event detection indicia, it would also be desirable to provide the cardiologist with information relating to cardiac event detection criteria, such as detection thresholds, and, where heart activity criteria must be met for cardioverting energy to be applied, indicia when such criteria are met would also be helpful. In the latter case, such indicia could facilitate parameter adjustment from default perimeter values to render successful therapy possible where such successful therapy may otherwise be unobtainable.

It would also be desirable for the cardiologist to be provided with more then one electrogram where more then

SUMMARY OF THE INVENTION

The invention therefore provides an implantable defibrillator for applying cardioverting electrical energy to a human heart. The defibrillator includes first sensing means for sensing electrical activity of the heart and generating a first electrogram, second sensing means for sensing electrical activity of the heart and generating a second electrogram, cardioverting means responsive to at least one of the first and second sensing means for applying the cardioverting electrical energy to the heart, and transmitting means for transmitting the first and second electrograms to a non-implantable external receiver. The present invention further provides a defibrillator systems for applying cardioverting electrical energy to a human heart. The system includes an implantable defibrillator including first sensing means for sensing electrical activity of the heart and generating a first electrogram, second sensing means for sensing electrical activity of the heart and generating a second electrogram, cardioverting means responsive to at least one of the first and second sensing means for applying the cardioverting electrical energy to the heart, and transmitting means for transmitting the first and second electrograms. The system further includes a non-implantable receiving means for receiving the first and second electrograms and including display means for simultaneously displaying the first and second electrograms.

The present invention still further provides a defibrillator system for applying cardioverting electrical energy to a human heart. The system includes an implantable defibrillator including sensing means for sensing electrical activity of the heart and generating an electrogram, and event detector having a threshold for detecting cardiac events in the electrogram, an event marker generator for generating event detection markers responsive to detection of the cardiac events, cardioverting means responsive to cardiac event detection for applying the cardioverting electrical energy to the heart and transmitting means transmitting the electrogram and the event detection markers. The system further includes a non-implantable receiving means for receiving the electrogram and the event detection markers, and display means for simultaneously displaying the electrogram, the threshold, and the event detection markers.

The present invention further provides a method for use in an implantable defibrillator for reporting the condition of a heart. The method includes the steps of sensing electrical activity of the heart and generating first and second electrograms, transmitting the first and second electrograms to an external non-implantable receiver, and receiving the first and second electrograms and simultaneously displaying the first and second electrograms.

The present invention further provides a method of verifying detection capability of an implantable defibrillator. The method includes the steps of, with the implantable defibrillator, sensing electrical activity of the heart and generating an electrogram, establishing a threshold and with the threshold, detecting cardiac events in the electrogram, generating an event detection marker with each detection of a cardiac event and transmitting the electrogram and the event detection markers to a non-implantable external receiver, and with the non-implantable receiver, receiving the electrogram and the event detection markers, and simultaneously displaying the electrogram, the threshold, and the event detection markers.

BRIEF DESCRIPTION OF THE DRAWINGS

The features of the present invention which are believed to be novel are set forth with particularity in the appended claims. The invention, together with further objects and advantages thereof, may best be understood by making reference to the following description in conjunction with the accompanying drawings, in the several figures of which like reference numerals identify identical elements, and wherein:

DETAILED DESCRIPTION OF THE PREFERRED EMBODIMENT

Figure 1:
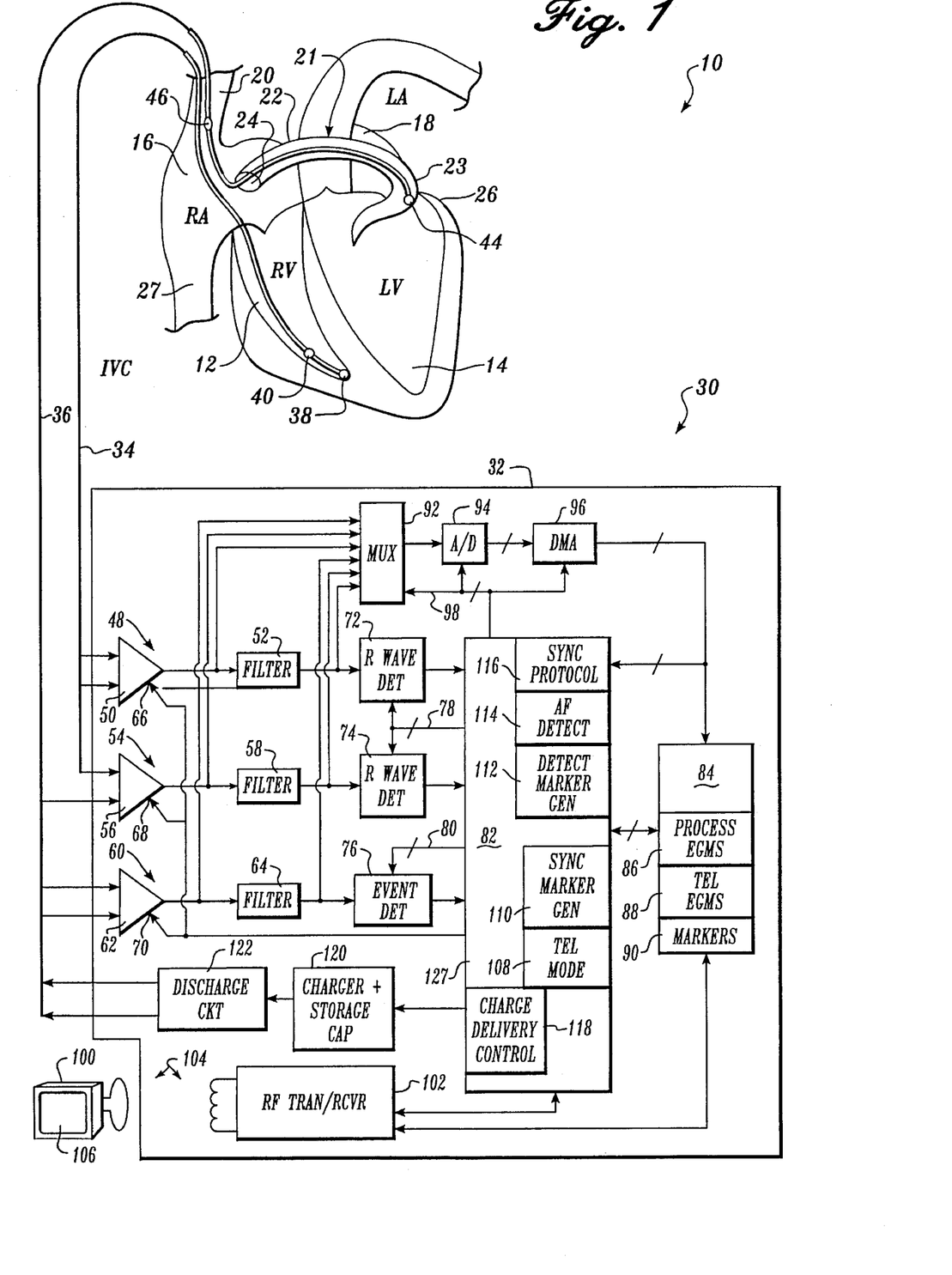
FIG. 1 is a schematic block diagram of a fully implantable automatic atrial defibrillator embodying the present invention.

Referring now to FIG. 1, it illustrates an atrial defibrillation system 30 embodying the present invention. The atrial defibrillation system 30 includes an implantable automatic atrial defibrillator 32 and an external programer 100.

The atrial defibrillator 32 includes an implantable lead system including an endocardial lead 34 and an intravascular lead 36. The endocardial lead has tip and ring electrodes 38 and 40 respectively adapted for placement in the right ventricle 12. The intravascular lead 36 has an elongated distal electrode 44 adapted for placement in the coronary sinus 22 or the great cardiac vein 23 and an elongated proximal electrode 46 adapted for placement in the superior vena cava 20 or right atrium 16. An alternative lead system may include separate leads for electrodes 44 and 46. This requires an additional endocardial lead (not shown in FIG. 1) adapted for placing electrode 46 in the superior vena cava 20 or the right atrium 16.

Electrodes 44 and 46 of lead 36 sense atrial activity of the heart. Electrodes 44 and 46 perform the additional function of applying cardioverting electrical energy across the atria 16 and 18 of the heart.

Electrodes 38 and 40 sense ventricular activity of the heart in the right ventricle. Electrode 44 together with either electrode 38 or electrode 40 also sense ventricular activity of the heart across the left ventricle. The dual sensing of ventricular activity is performed for the purpose of reliably sensing R waves of the heart as fully described in U.S. Pat. No. 5,348,021 issued on Sep. 20, 1994 for APPARATUS AND METHOD FOR RELIABLY DETECTING A DEPOLARIZATION ACTIVATION WAVE OF THE HEART AND ATRIAL DEFIBRILLATOR UTILIZING SAME, and which is assigned to the assignee of the present invention and incorporated herein by reference. The dual ventricular activity sensing further serves to support dual reset of an interval timer employed during cardioverting energy application synchronization as described in co-pending U.S. application Ser. No. 08/259,515, now U.S. Pat. No. 5,464,433, filed Jun. 14, 1994 for ATRIAL DEFIBRILLATOR AND METHOD FOR PROVIDING DUAL RESET OF AN INTERVAL TIMER, and which is assigned to the assignee of the present invention and incorporated herein by reference.

The atrial defibrillator 32 also includes a right ventricular (RV) sense channel 48 including sense amplifier 50 and filter 52, a right ventricular to coronary sinus (RVCS) sense channel 54 including sense amplifier 56 and filter 58 and an atrial (RACS) sense channel 60 including sense amplifier 62 and filter 64. Sense amplifier 50 is coupled to electrodes 38 and 40 of lead 34 in the right ventricle and sense amplifier 56 is coupled to electrode 44 of lead 36 in the coronary sinus/great cardiac vein and to either electrode 38 or electrode 40 of lead 34 in the right ventricle. Sense amplifier 60 is coupled to electrode 46 in the right atrium or superior vena cava and to electrode 44 in the coronary sinus/great cardiac vein.

Each sense channel provides two electrograms, a direct electrogram and a filtered (differentiated) electrogram. To that end, the RV channel 48 provides a direct electrogram (RV direct) at the output of sense amplifier 50 and a filtered electrogram (RV filtered) at the output of filter 52. Similarly, the RVCS channel 54 and the RACS channel 60 provide direct electrograms at the outputs of sense amplifiers 56 and 62 respectively (RVCS direct, RACS direct) and filtered electrograms (RVCS filtered, RACS filtered) at the outputs of the filters 58 and 64 respectively. As will be appreciated by those skilled in the art, the sense amplifiers 50, 56, and 62 may include some internal filtering. Such sense amplifiers including such internal filtering are also contemplated herein as providing the direct electrograms at their outputs.

Each of the sense amplifiers 50, 56, and 62 includes a gain control input 66, 68, and 70 respectively. The gain control inputs permit the gain of each of the amplifiers to be adjusted to maintain a desired sense margin as disclosed in co-pending U.S. application Ser. No. 08/213,119, now U.S. Pat. No. 5,458,621, filed Mar. 15, 1994 for AUTOMATIC GAIN CONTROL AND METHOD FOR ENABLING DETECTION OF LOW AND HIGH AMPLITUDE DEPOLARIZATION ACTIVATION WAVES OF THE HEART AND ATRIAL DEFIBRILLATOR UTILIZING THE SAME, and which application is assigned to the assignee of the present invention and incorporated herein by reference, or to otherwise optimize a desired sensing or detection characteristic.

The atrial defibrillator 32 further includes three hardware cardiac event detectors; R wave detector 72, R wave detector 74, and event detector 76. The R wave detectors 72 and 74 each have a detection threshold which may be individually controlled over a control bus 78. When the filtered electrograms of the RV and RVCS channels exceed the respective thresholds of R wave detectors 72 and 74, an RV detect is noted as will be described subsequently.

Similarly, the event detector 76 has a threshold which may be controlled by control bus 80. When the filtered RACS electrogram exceeds this threshold, an atrial event is noted as will be described subsequently.

The atrial defibrillator 32 further includes a microprocessor 82 and a memory 84. The microprocessor controls the overall functioning of the atrial defibrillator under software controlled by operating instructions stored in the memory 84. In addition to storing operating instructions, the memory also stores process electrograms in a portion 86, telemetry electrograms in a portion 88, and detection and synchronization markers in a portion 90. The process electrograms are electrogram data samples acquired during data acquisition periods which enable the detection of atrial fibrillation. The telemetry electrograms are electrogram data samples of electrograms to be transmitted to the receiver of an external, non-implanted programmer. As will be seen hereinafter, in accordance with the present invention, multiple electrograms may be transmitted to an external programmer for simultaneous display along with cardiac event detection and/or synchronization markers stored in memory portion 90. The cardiac event detection markers indicate the fact and timing of cardiac event detection. As will also be seen hereinafter, the synchronization markers indicate those heart intervals in which the patient's heart activity satisfies energy delivery criteria. That criteria, in accordance with this preferred embodiment, includes multiple criteria including dual R wave detection in both the RV and RVCS channels and interval duration criteria.

To store the electrogram data in the memory 84, the atrial defibrillator 32 further includes a multiplexor 92, an analog-to-digital converter 94, and a direct memory access controller 96. The microprocessor controls the multiplexor 92, analog-to-digital converter 94, and direct memory access controller 96 over a control bus 98 to configure the same for supplying and storing the electrogram data in memory 84 necessary to fulfill a desired function. For example, in one telemetry mode of operation, digital samples of any three of the direct and filtered electrograms may be stored in the telemetry electrogram portion 88. In a synchronization mode, digital samples of the RV and RVCS direct electrograms may be stored in memory portion 88 and the R wave detection markers and synchronization markers may be stored in portion 90. The digital samples or data stored in portion 88 is only temporarily stored therein before it is transmitted to the external programmer for display. In still another telemetry mode, digital samples of the RACS direct electrogram and digital samples of the RV direct electrogram are stored in memory portion 88 temporarily prior to transmission. Also stored in memory portion 90 are the R wave detection markers for the RV direct electrogram and the event detection markers from the RACS direct electrogram.

A transmitter/receiver 102 within the atrial defibrillator 32 transmits the electrograms to the external non-implanted programer 100. The transmitter/receiver 102 and external programer 100 form a telemetry system 104 which preferably takes the form of the telemetry system fully described in U.S. Pat. No. 5,342,408, issued Aug. 30, 1994, for TELEMETRY SYSTEM FOR AN IMPLANTABLE CARDIAC DEVICE, which is assigned to the assignee of the present invention and incorporated herein by reference. The external controller 100 includes a display 106 for displaying the electrograms and other required indicia. Displays which may be achieved in accordance with the present invention will be more particularly described in connection with FIGS. 3–7.

The microprocessor 82 forms a number of functional stages in operating under operating instructions acquired from the memory 84. Those functional stages include a telemetry mode stage 108, a synch marker generator 110, a detection marker generator 112, an atrial fibrillation detector 114, a synchronization protocol stage 116, and a charge and energy delivery control stage 118.

The telemetry mode stage 108 sets the atrial defibrillator 32 in the proper telemetry mode for configuring the multiplexor 92, the analog to digital converted 94, and the direct memory access controller 96. The external programer 100 transmits programming parameters and other data to the transmitter/receiver 102. That other data may include telemetry commands for selecting any one of the telemetry modes previously described and to be described in more detail hereinafter.

The detection marker generator stage 112 generates the detection markers for storage in memory portion 90. When a cardiac event is detected by R wave detector 72, detection 74 or event detector 76, the detection marker generator 112 time stamps and stores indicia of the same in memory portion 90 to be later associated with its corresponding electrogram for display. Alternatively, the indicia may be stored in a sequential array which when accessed for telemetry, will be in proper time relation to its corresponding electrogram. The indicia are stored in locations which correspond in time to the points of their corresponding electrograms where the events where detected. As a result, when the markers are displayed along with their corresponding electrograms, the points in the electrograms where detection occurred may be readily identified.

The synch marker generator stage 110 performs a similar function. When the synchronization protocol stage 116 determines that all of the criteria for energy delivery are satisfied by the RV and RVCS electrograms during a cardiac interval, the marker generator 112 generates a synchronization time stamp for storage in memory portion 90 by the microprocessor 82. When the synchronization markers are displayed along with the RV and RVCS electrograms, the heart intervals satisfying the synchronization criteria may be readily identified. More importantly, the synchronization markers will enable the cardiologist to identify those intervals which do not satisfy the energy delivery criteria and the electrograms for those intervals will illustrate heart activity morphology to enable the cardiologist to diagnosis the cause for the criteria not being satisfied for those intervals. As previously mentioned, such criteria may include the synchronization criteria disclosed in the aforementioned application Ser. No. 08/259,476.

If atrial fibrillation is detected, a charge and delivery control 118 causes a charger circuit 120 to charge a storage capacitor therein to a selected peak voltage. The charge and delivery control 118 monitors the charging of the capacitor. It terminates the charging when the voltage across the storage capacitor has reached the selected peak voltage.

Thereafter, upon the successful completion of the synchronization protocol by the synchronization protocol stage, the charge and delivery control 118 causes a discharge circuit 122, which is coupled to the storage capacitor of circuit 120, to discharge a portion of the energy stored in the storage capacitor. The discharged energy is applied to electrodes 44 and 46 of intravascular lead 36 for applying the cardioverting electrical energy to the atria 16 and 18 of the heart 10.

The entire cardioversion sequence from original detection of an atrial fibrillation episode through successful cardioversion is preferably initiated at spaced apart predetermined times as fully described in co-pending U.S. application Ser. No. 08/232,767, now U.S. Pat. No. 5,464,432, filed Apr. 25, 1994 for AN IMPLANTABLE ATRIAL DEFIBRILLATOR HAVING AN INTERMITTENTLY ACTIVATED FIBRILLATION DETECTOR, which application is assigned to the assignee of the present invention and incorporated herein by reference. As described therein, under the control of a wake up timer, the atrial defibrillator 32 may be activated at spaced apart times for the detection and cardioversion of atrial fibrillation. Under this methodology, atrial fibrillation detection may be initiated once every minute to once every two hours, for example, in order to conserve the power of a battery (not shown). When the atrial defibrillator is activated to detect for an atrial fibrillation episode, the microprocessor 82 is first activated to activate the sense amplifiers 50 and 62, the multiplexor 92, the analog to digital converter 94, the direct memory access controller 96, and the memory 84 to initiate an eight second data acquisition period. During this acquisition period, the microprocessor 82 causes the multiplexor 92 to alternately couple the outputs of sense amplifiers 50 and 62 to the analog to digital converter 94 to permit the storing of digital samples of the electrograms sense by electrodes 44 and 46 of lead 36 and electrodes 38 and 40 of lead 34. The electrogram digital samples for the entire eight seconds are stored in the process memory portion 86 of the memory 84.

When the eight second acquisition is completed, the microprocessor 82 implements the atrial fibrillation detector 114 by processing the data stored in the process memory portion 86 to detect for atrial fibrillation in accordance with an atrial fibrillation detection algorithm and more particularly and preferably in accordance the atrial fibrillation detectors disclosed in the aforementioned copending U.S. applications Ser. Nos. 08/233,251, now U.S. Pat. No. 5,522,852, or 08/278,055, now U.S. Pat. No. 5,486,199. If atrial fibrillation is not detected, the atrial defibrillator is deactivated until the next predetermined time.

If atrial fibrillation is detected by the atrial fibrillation detector 114, the charge delivery control 118 causes the charge and storage capacitor circuit 120 to charge the storage capacitor to a preselected peak voltage. When the capacitor is charged, the atrial fibrillation detector 114 determines if the atria 16 and 18 of heart 10 are still in fibrillation. In doing so, the atrial defibrillator will perform another eight second data acquisition as previously described.

If the atria are not still in fibrillation, the process is completed and the atrial defibrillator is deactivated until the next predetermined time. However, if the atria are still in fibrillation, the microprocessor 82 then implements the synchronization protocol 116. In performing the synchronization protocol, the multiplexor 92, analog-to-digital converter 94 and direct memory access controller 96 are configured to provide electrograms from the RV and RVCS channels to the memory. These electrograms may be stored for later use as described in co-pending application Ser. No. 08/264,319, now U.S. Pat. No. 5,522,850, filed Jun. 23, 1994, for SELECTIVE DATA STORAGE FOR AN AUTOMATIC IMPLANTABLE ATRIAL DEFIBRILLATOR, which application is assigned to the assignee of the present invention and incorporated herein by reference. The electrograms may also be, in accordance with the present invention, stored in memory portion 88 for transmission to the external programer for display on the display 106. The synchronization protocol, in accordance with the aforementioned co-pending application Ser. No. 08/259,476, may require an R wave to be detected in both the RV and RVCS channels by detectors 72 and 74 respectively. The synchronization protocol may also require cardiac intervals to be longer then a preselected minimum interval as described in the aforementioned U.S. Pat. No. 5,207,219. The synchronization protocol may require other criteria to be met and, to that end, acquires electrogram data directly from the direct memory access controller 96 when the data is transferred to the memory 84. When the synchronization protocol criteria are met, the synchronization marker generator 110 generates and time stamps a synchronization marker and causes the discharge circuit 122 to discharge a portion of the energy stored in the storage capacitor of circuit 120 between electrodes 44 and 46 for cardioverting the atria of the heart. Following the delivery of the cardioverting electrical energy to the atria, the atrial fibrillation detector 114 will once again determine if atrial fibrillation is still present. In doing so, a further eight second data acquisition is performed. If the atria have been successfully cardioverted, the process is completed and the atrial defibrillator is deactivated until the next predetermined time. If the heart is still in atrial fibrillation, the cardioversion process is repeated at preferably a higher voltage.

Figure 2:
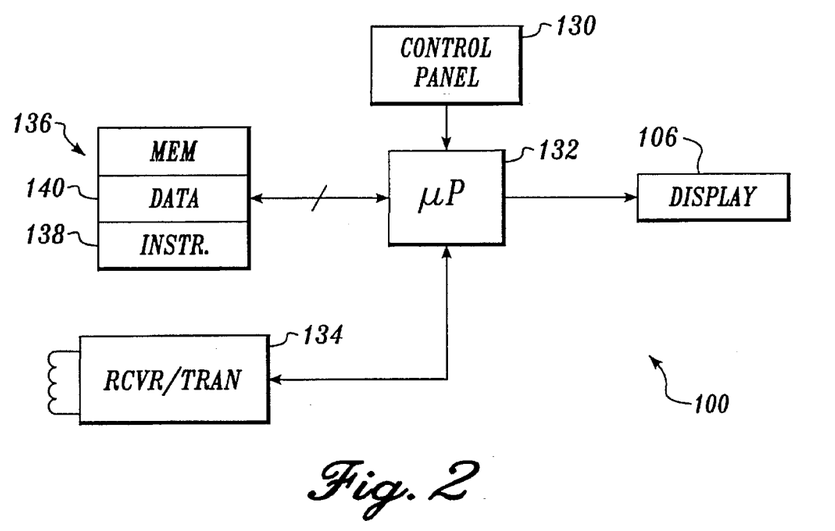
FIG. 2 is a schematic block diagram of an external receiver for simultaneously displaying a plurality of electrograms together with corresponding defibrillator verifying information.

Referring now to FIG. 2, it illustrates the external programmer 100 of FIG. 1 in simplified block diagram form. The programer includes a control panel 130, a display 106, a microprocessor 132, a transmitter/receiver 134, and a memory 136.

The memory 136 includes an instruction portion 138 and a data portion 140. The data portion 140 may store operating parameters of the defibrillator with which its receiver/ transmitter 134 is communicating and configuration data corresponding to each different atrial defibrillator with which its receiver/transmitter may communicate.

The control panel 130 is provided to enable selection of programmable parameters and operating functionality of atrial defibrillator 32. To that end, the control panel may be used to select a desired electrogram display mode. Examples of some of the displays obtainable from the selectable display modes will be described with respect to FIGS. 3–7.

The receiver/transmitter 134 is preferably arranged as disclosed in the aforementioned U.S. Pat. No. 5,342,408 for receiving and transmitting serial data. When serial electrogram data to be displayed is received by the receiver/ transmitter 134, the microprocessor preferably temporarily stores it in data portion 140 before it is displayed. After a short delay of, for example, two seconds, the electrogram data received from the implanted defibrillator is addressed by the microprocessor and displayed on the display 106. Even though more then one electrogram may be displayed at a time, the microprocessor processes the data fast enough in a manner known in the art so that, as will be seen in FIGS. 3–7, the multiple electrograms may not only be simultaneously displayed all at once on the same display, but preferably vertically arrayed and aligned in time alignment as well. When the event detection and/or synchronization markers are included in the displays, they may also be in time alignment with the electrograms so that the points in the electrograms where event detection and synchronization occur may be readily and visually determined. Although the electrogram samples and markers are temporarily stored in memory portions 88 and 90 of memory 84, for, for example two seconds, prior to transmission to external programmer 100 and temporarily stored in portion 140 of memory 136, for, for example two seconds, prior to being displayed on display 106, once electrogram display begins, the running display will be continuous but delayed by four seconds so as to have the appearance of being a real time display. The temporary data storage, resulting in delay, is provided to permit data formatting for transmission, data formatting for display, and collection of sufficient data in both the implanted defibrillator and at the external programer to assure a continuous and uninterrupted running display once electrogram display is commenced.

Figure 3:
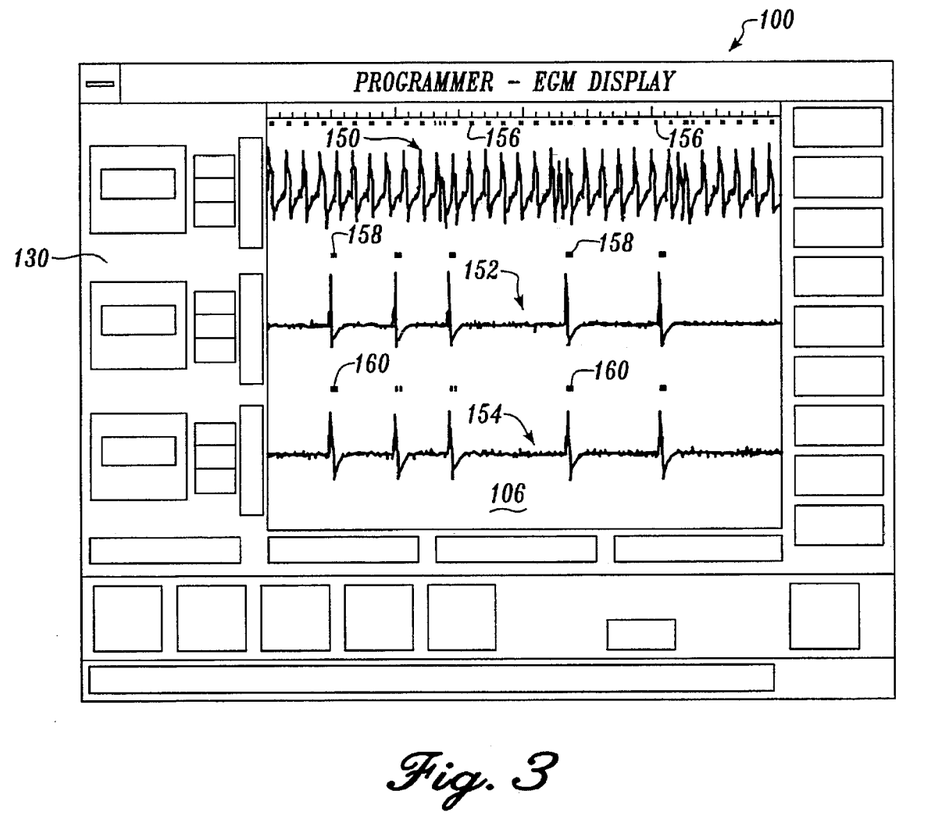
FIG. 3 illustrates a plurality of electrograms with corresponding cardiac event detection markers in accordance with the present invention.

Referring now to FIG. 3, it illustrates a typical electrogram display obtainable when the implantable defibrillator is programmed in a three-channel display mode. All three electrograms displayed on the display 106 are direct electrograms. The control panel 130 of the programmer 100 borders the display 106 along the left side, the right side, and the bottom of the display 106.

The top electrogram 150 is the electrogram from the atrial or RACS channel 60 taken at the output of sense amplifier 62. The middle electrogram 152 is the electrogram from the RVCS channel 54 taken at the output of sense amplifier 56. The bottom electrogram 154 is the electrogram from the RV channel 48 taken at the output of sense amplifier 50. When these electrograms are selected, the telemetry mode stage 108 configures the multiplexor 92 to sequentially couple the outputs of the sense amplifiers 50, 56, and 62 to the analog-to-digital converter 94. The data samples thus generated by the analog-to-digital converter 94 are then conveyed to the direct memory access controller 96 which then stores them in their proper locations in memory portion 88. Also shown in FIG. 3 are the event detection markers 156, 158, and 160 associated with each of the electrograms 150, 152 and 154 respectively. Like the electrograms, the markers 156, 158 and 160 are aligned in time relation to their respective electrograms and hence to each other.

The display of FIG. 3 enables the cardiologist to quickly determine the condition of the patient's heart by displaying a direct electrogram for the atria and each ventricle. The markers 156, 158, and 160 will also verify that electrogram signal levels are adequate to permit electrogram event detection. Further, the relative number of the event detection markers in the RACS channel electrogram 150 during each cardiac interval can be used to provide a quick visual indication of a possible atrial fibrillation episode.

Figure 4:
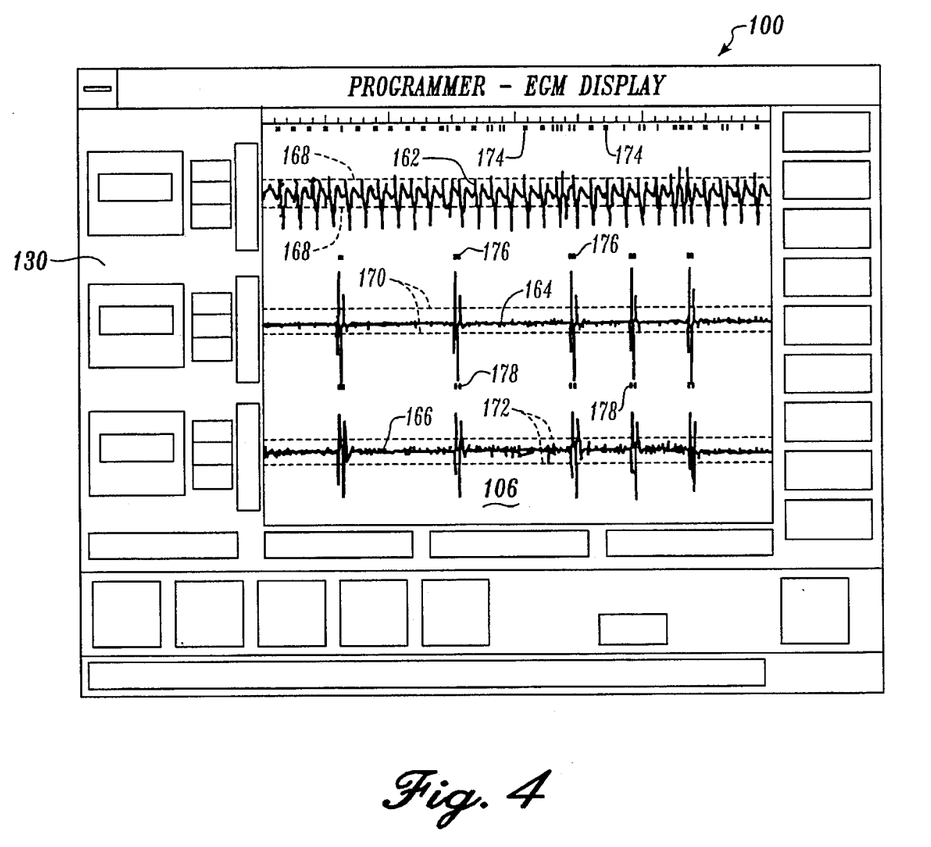
FIG. 4 illustrates a plurality of electrograms with corresponding cardiac event detection markers and cardiac event detection thresholds in accordance with the present invention.

Referring now to FIG. 4, it illustrates another electrogram display obtainable when the implantable defibrillator is programed in a three-channel display mode. Here, all three electrograms displayed on the display 106 are filtered electrograms.

The top electrogram 162 is the electrogram from the atrial or RACS channel 60 taken at the output of filter 64. The middle electrogram 164 is the electrogram from the RVCS channel 54 taken at the output of filter 58. The bottom electrogram 166 is the electrogram from the RV channel 48 taken at the output of filter 52. When these electrograms are selected, the telemetry mode stage 108 configures the multiplexor 92 to sequentially couple the outputs of filters 52, 58 and 64 to the analog-to-digital converter 94. The data samples thus generated are then conveyed to the direct memory access controller 96 which then stores them in their proper location in memory portion 88. Also shown in FIG. 4 are the event detection thresholds 168, 170, and 172 and markers 174, 176 and 178 associated with each of the electrograms 162, 164 and 166 respectively. The thresholds may be obtained from the portion 140 of memory 136 in response to the implanted device transmitting its serial number or model number to the programer. The programer may then access a look-up table in data portion 140 to obtain the thresholds to display. Alternatively, the implanted device may transmit the thresholds to the programmer along with its other programed parameters when communication is initiated between the programmer and the implanted defibrillator. By either method, the implantable defibrillator may be arranged to transmit data indicative of the threshold of the R wave detectors 72 and 74 and event detector 76 so that the programmer may display the proper thresholds responsive to the transmitted data.

The display of FIG. 4 enables the cardiologist to determine if adequate electrogram signal levels are present to permit electrogram event detection by the R wave detectors 72 and 74 and the event detector 76. If events are not being detected in one or more of the channels, the cardiologist is then able to increase the gain of the appropriate sense amplifiers 50, 56, or 62 through programming to permit adequate sensing. Adequate detection can then be readily verified.

Figure 5:
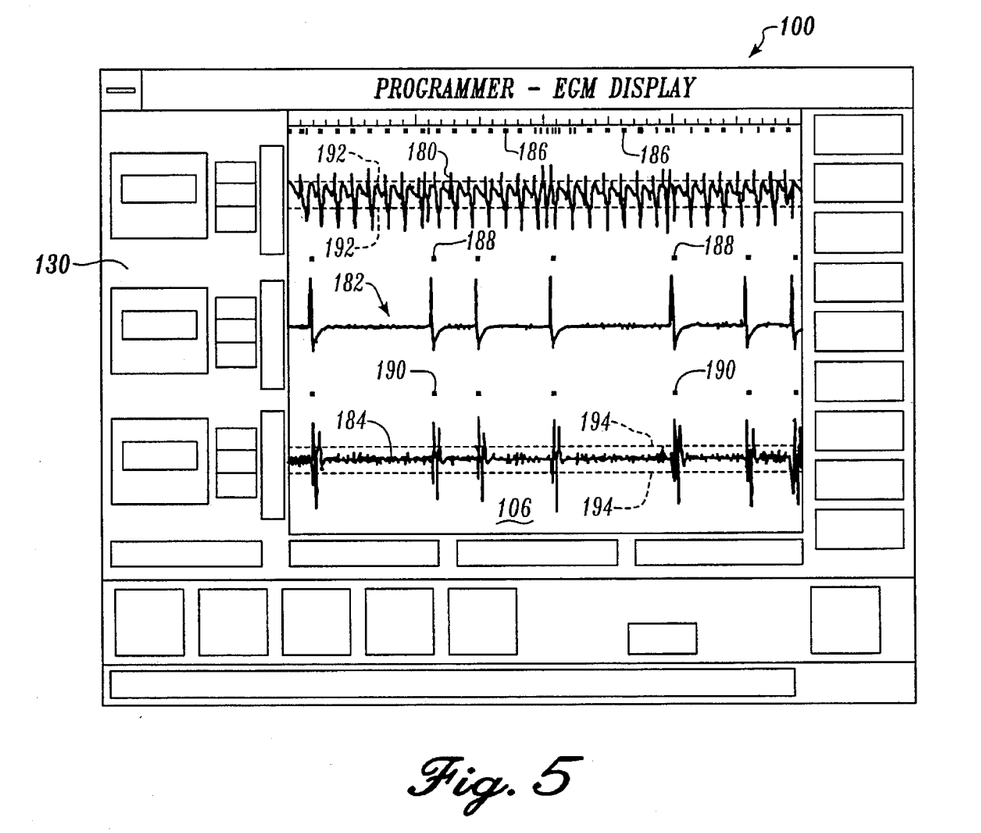
FIG. 5 illustrates a plurality of electrograms wherein two of the electrograms are illustrated with corresponding cardiac event detection markers and cardiac event detection thresholds and illustrating another one of the electrograms with its corresponding cardiac event detection markers without detection thresholds in accordance with the present invention.

Referring now to FIG. 5, it illustrates another electrogram display obtainable when the implanted defibrillator is programed in a three-channel display mode. Here, two electrograms displayed on the display 106 are filtered electrograms and one electrogram displayed on the display 106 is a direct electrogram. The top electrogram 180 is a filtered electrogram from the atrial or RACS channel 60 taken at the output of filter 64. The middle electrogram 182 is a direct electrogram from the RVCS channel 54 taken at the output of the sense amplifier 56. The bottom electrogram 184 is a filtered electrogram from the RV channel 48 taken at the output of filter 52. When these electrograms are selected, the telemetry mode stage 108 configures the multiplexor 92 to sequentially couple the outputs of the filters 52 and 64 and the output of sense amplifier 56 to the analog-to-digital converter 94. The data samples thus generated are then conveyed to the direct memory access controller 96 which then stores them in their proper locations in memory portion 88. Also shown in FIG. 5 are the event detection markers 186, 188, and 190 associated with each of the electrograms 180, 182 and 184 respectively and the thresholds 192 and 194 of event detector 76 and R wave detector 72 respectively.

Figure 6:
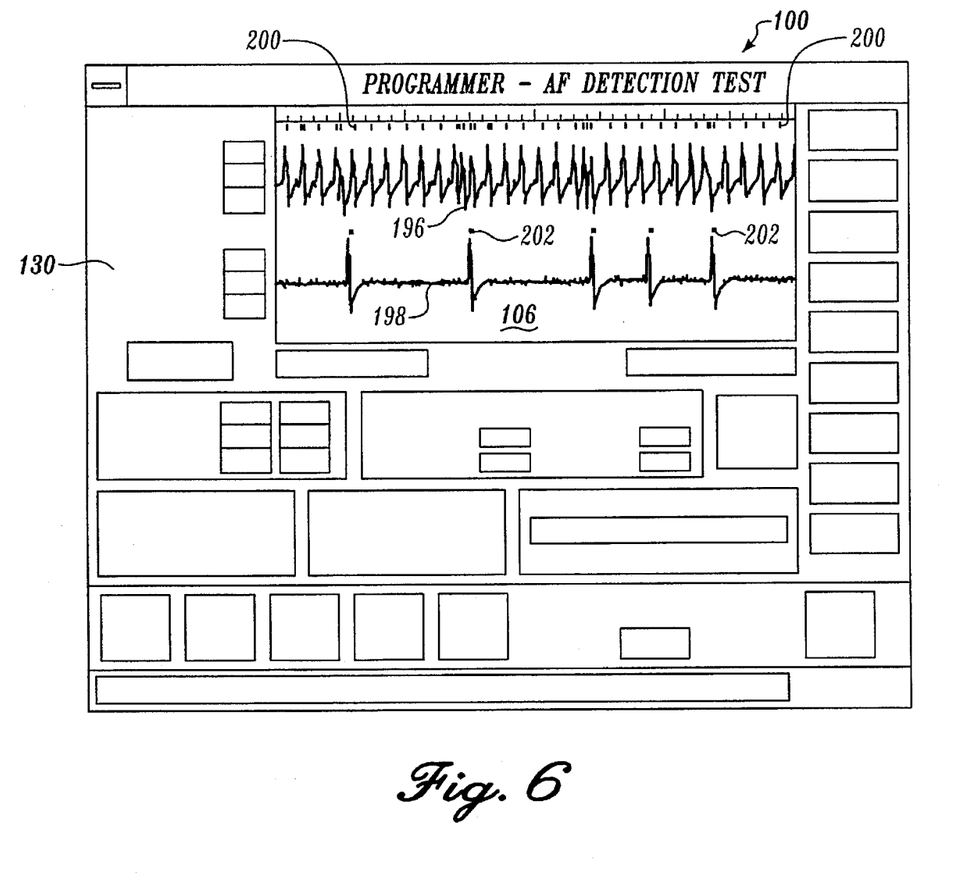
FIG. 6 illustrates an electrogram of atrial activity together with its corresponding cardiac event detection markers and another electrogram of ventricular activity illustrated with its corresponding cardiac event detection markers in accordance with the present invention.

Referring now to FIG. 6, it illustrates a typical electrogram display which may be obtained when the implantable defibrillator is programed in an atrial fibrillation detection evaluation mode. Here, two electrograms are displayed on the display 106. One electrogram 196 is a direct electrogram from the atrial or RACS channel 60 taken at the output of sense amplifier 62. The other electrogram 198 is a direct electrogram from the RV channel 48 taken at the output of sense amplifier 50. When this mode is selected, the telemetry mode stage 108 configures the multiplexor 92 to sequentially couple the outputs the sense amplifiers 50 and 62 to the analog-to-digital converter 94. The data samples are then stored in memory portion 88 as previously described. Also shown in FIG. 6 are the event detection markers 200 and 202 associated with electrograms 196 and 198 respectively. Again, the electrograms 196 and 198 and the markers 200 and 202 are aligned in time relation to each other.

The display of FIG. 6 enables the cardiologist to visually observe the electrograms utilized by the atrial defibrillator 32 during atrial defibrillation detection. The markers 200 and 202 may be utilized to verify that electrogram signal levels are sufficient to permit electrogram event detection and hence atrial fibrillation detection by the atrial defibrillator. Again, the relative number of event detections in the RACS channel electrogram 196 during each cardiac interval between the detection markers 202 can be used to indicate a possible atrial fibrillation episode.

Figure 7:
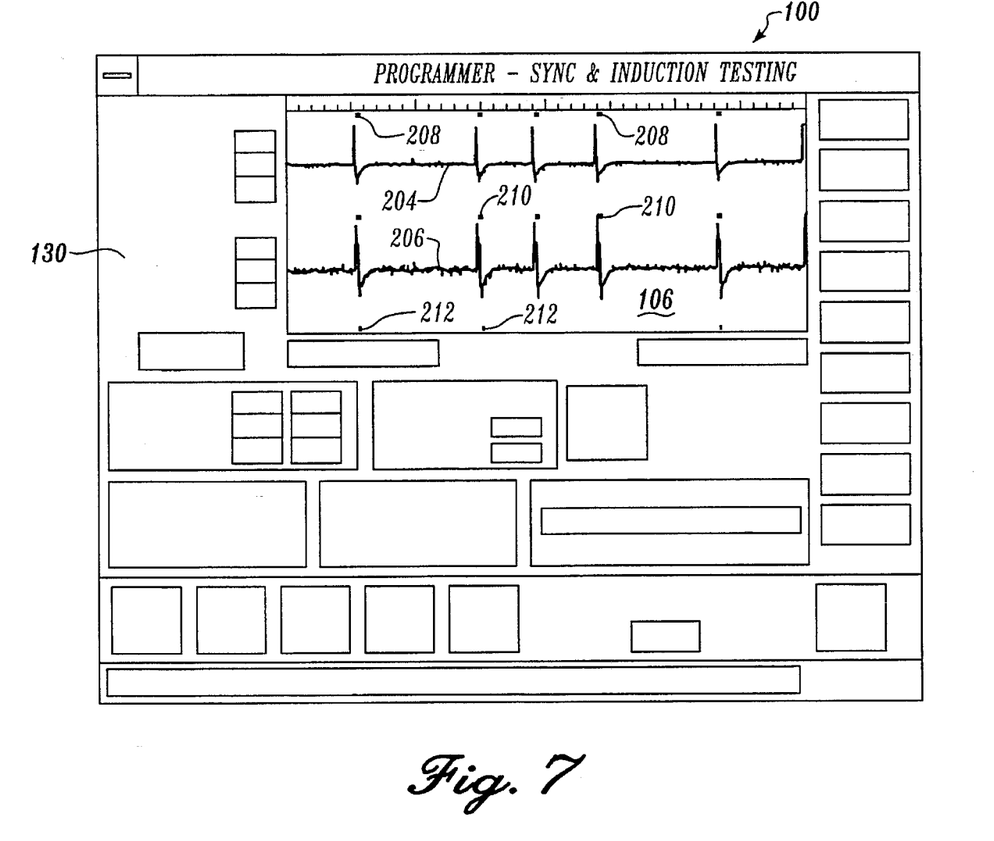
FIG. 7 illustrates a pair of electrograms of ventricular activity shown with their corresponding cardiac event detection markers and with synchronization markers indicating when cardioverting energy delivery criteria are satisfied in accordance with the present invention.

Referring now to FIG. 7, it illustrates a typical electrogram display obtainable when the implanted defibrillator is programed in an energy delivery synchronization mode. Here, two electrograms are displayed on the display 106. One electrogram 204 is a direct electrogram from the RVCS channel 54 taken at the output of sense amplifier 56. The other electrogram 206 is a direct electrogram from the RV channel 48 taken at the output of sense amplifier 50. When these electrograms are selected, the telemetry mode stage 108 configures the multiplexor 92 to sequentially couple the outputs of the sense amplifiers 56 and 62 to the analog-to-digital converter 94. The digital samples thus generated are then stored in the memory 88 as previously described. Also shown in FIG. 7 are the event detection markers 208 and 210 associated with the electrograms 204 and 206 respectively. Again, the electrograms and the markers are aligned in time relation to each other.

Also displayed in the display of FIG. 7 are the synchronization marker 212 which indicate those cardiac intervals in which the heart activity satisfies the synchronization criteria and hence those times when the cardioverting energy could be safely applied to the heart. As perviously mentioned, that criteria preferably includes the sensing of an R wave in both the RV and RVCS channels (a condition satisfied by all of the intervals displayed in FIG. 7) and a cardiac interval being longer then a predetermined interval (a condition not satisfied by all of the intervals displayed in FIG. 7). The display of FIG. 7 provides verification that the patient's heart activity together with the programmable parameters programed into the implanted device will result in the application of cardioverting energy to the patient's heart once fibrillation is detected.

While a particular embodiment of the present invention has been shown and described, modifications may be made. For example, while detection thresholds have been associated with filtered electrograms herein, such detection thresholds could also be associated with direct electrograms as well. Hence, the term electrogram, unless otherwise specified, is meant to denote either a filtered or a direct electrogram as described herein. Also, the electrograms may be more permanently stored in data memory portion 140 for later simultaneous display. Further, while the electrogram telemetry system of the present invention has been disclosed in connection with an implantable atrial defibrillator, it could be implemented in other forms of implantable cardiac therapeutic devices as well wherein verification of energy delivery is important or wherein electrograms from multiple sense channels and/or heart chambers are required for proper device functionality, cardiac condition diagnosis, and/or treatment. It is therefore intended to cover in the appended claims all such changes and modification which fall within the true spirit and scope of the invention.

What is claimed is:

1. An implantable defibrillator for applying cardioverting electrical energy to a human heart, said defibrillator comprising:

first sensing means for sensing electrical activity of the heart and generating first electrogram data representing a first electrogram;

second sensing means for sensing electrical activity of the heart and generating second electrogram data representing a second electrogram;

cardioverting means responsive to at least one of the first and second sensing means for applying the cardioverting electrical energy to the heart;

formatting means for formatting the first and second electrogram data for combined transmission; and transmitting means for transmitting the formatted first and second electrogram data to a nonimplantable external receiver for simultaneous display of the first and second electrograms.

2. A defibrillator as defined in claim 1 further including third sensing means for sensing electrical activity of the heart and generating a third electrogram, and the transmitting means for transmitting the third electrogram with the first and second electrograms to a nonimplantable external receiver.

3. A defibrillator as defined in claim 1 further including a memory for temporarily storing the first and second electrograms and means for conveying the first and second electrograms from the memory to the transmitting means.

4. An implantable defibrillator for applying cardioverting electrical energy to a human heart, said defibrillator comprising:

first sensing means for sensing electrical activity of the heart and generating a first electrogram;

second sensing means for sensing electrical activity of the heart and generating a second electrogram;

cardioverting means responsive to at least one of the first and second sensing means for applying the cardioverting electrical energy to the heart;

a first event detector for detecting cardiac events in the first electrogram;

a second event detector for detecting cardiac events in the second electrogram;

detection marker generating means for generating first and second cardiac event detection markers when the first and second event detectors respectively detect said cardiac events in the first and second electrograms; and transmitting means for transmitting the first and second electrograms and at least one of the first and second cardiac event detection markers with a corresponding one of the first and second electrograms to a nonimplantable external receiver.

5. A defibrillator as defined in claim 4 further including electrogram analyzing means for determining if corresponding cardiac cycles of the first and second electrograms satisfy a synchronization criteria and synchronizing means for providing a synchronization marker whenever corresponding cardiac cycles of the first and second electrograms satisfy the synchronization criteria, the transmitting means for transmitting the synchronization markers with the electrograms and the cardiac event detection markers.

6. A defibrillator system for applying cardioverting electrical energy to a human heart, said system comprising:

an implantable defibrillator including first sensing means for sensing electrical activity of the heart and generating first electrogram data representing a first electrogram, second sensing means for sensing electrical activity of the heart and generating second electrogram data representing a second electrogram, cardioverting means responsive to at least one of the first and second sensing means for applying the cardioverting electrical energy to the heart, first formatting means for formatting the first and second electrogram data for combined transmission, and transmitting means for transmitting the formatted first and second electrogram data; and nonimplantable receiving means for receiving the formatted first and second electrogram data and including second formatting means for reformatting the received formatted first and second electrogram data and display means responsive to the reformatted first and second electrogram data for simultaneously displaying the first and second electrograms in time aligned relation.

7. A system as defined in claim 6 wherein said defibrillator further includes a memory for temporarily storing the first and second electrograms and means for conveying the first and second electrograms from the memory to the transmitting means.

8. A system as defined in claim 6 wherein said defibrillator further includes third sensing means for sensing electrical activity of the heart and generating a third electrogram, and the transmitting means for transmitting the third electrogram with the first and second electrograms, and the display means of the nonimplantable receiving means simultaneously displaying the third electrogram with the first and second electrograms.

9. A defibrillator system for applying cardioverting electrical energy to a human heart, said system comprising:

an implantable defibrillator including first sensing means for sensing electrical activity of the heart and generating a first electrogram, second sensing means for sensing electrical activity of the heart and generating a second electrogram, cardioverting means responsive to at least one of the first and second sensing means for applying the cardioverting electrical energy to the heart, a first event detector for detecting cardiac events in the first electrogram, a second event detector for detecting cardiac events in the second electrogram, detection marker generating means for generating first and second cardiac event detection markers when the first and second event detectors respectively detect said cardiac events in the first and second electrograms, and transmitting means for transmitting the first and second electrograms and at least one of the first and second cardiac event detection markers with a corresponding one of the first and second electrograms; and nonimplantable receiving means for receiving the first and second electrograms and including display means for simultaneously displaying the first and second electrograms and the at least one of the first and second cardiac event detection markers with the corresponding one of the first and second electrograms display means simultaneously displaying the first and second electrograms.

10. A system as defined in claim 9 wherein the first and second event detectors include means for establishing first and second detection thresholds respectively, and the display means for displaying at least one of the first and second detection thresholds simultaneously with the corresponding one of the first and second electrograms and first and second cardiac event detection markers.

11. A system as defined in claim 10 wherein said transmitting means includes means for transmitting data indicative of the first and second detection thresholds and wherein the display means includes means for displaying the at least one of the first and second detection thresholds responsive to said data.

12. A system as defined in claim 9 wherein the defibrillator further includes electrogram analyzing means for determining if corresponding cardiac cycles of the first and second electrograms satisfy a synchronization criteria and synchronizing means for providing a synchronization marker whenever corresponding cardiac cycles of the first and second electrograms satisfy the synchronization criteria, the transmitting means for transmitting the synchronization markers with the first and second electrograms, and the display means for displaying the synchronization markers simultaneously with the first and second electrograms and the at least one of the first and second cardiac event detection markers.

13. A defibrillator system for applying cardioverting electrical energy to a human heart, said system comprising:

an implantable defibrillator including sensing means for sensing electrical activity of the heart and generating an electrogram;

an event detector having a threshold for detecting cardiac events in the electrogram, an event marker generator for generating event detection markers responsive to detection of said cardiac events, cardioverting means responsive to cardiac event detection for applying the cardioverting electrical energy to the heart, and transmitting means for transmitting the electrogram and the event detection markers;

nonimplantable receiving means for receiving the electrogram and the event detection markers; and display means for simultaneously displaying the electrogram, the threshold, and the event detection markers.

14. A system as defined in claim 13 wherein said defibrillator further includes a memory for temporarily storing the electrogram and the event detection markers and means for conveying the electrogram and event detection markers from the memory to the transmitting means.

15. A system as defined in claim 13 wherein said transmitting means includes means for transmitting data indicative of the threshold and wherein the display means includes means for displaying the threshold responsive to said data.

16. In an implantable defibrillator, a method of reporting the condition of a heart, said method including the steps of:

sensing electrical activity of the heart and generating first and second electrogram data representing first and second electrograms respectively;

formatting the first and second electrogram data for combined transmission;

transmitting the formatted first and second electrogram data to an external nonimplantable receiver;

receiving the first and second formatted electrogram data;

reformatting the received formatted electrogram data for simultaneous display; and simultaneously displaying the first and second electrograms.

17. A method as defined in claim 16 including the further steps of generating third electrogram data representing a third electrogram, formatting the third electrogram data with the first and second electrogram data for combined transmission, transmitting the third electrogram data with the first and second electrogram data, receiving the formatted first, second, and third electrogram data, reformatting the formatted first, second and third electrogram data for simultaneous display, and displaying the third electrogram simultaneously with the first and second electrograms.

18. In an implantable defibrillator, a method of reporting the condition of a heart, said method including the steps of:

sensing electrical activity of the heart and generating first and second electrograms;

detecting cardiac events in the first electrogram;

detecting cardiac events in the second electrogram;

generating first and second cardiac event detection markers upon detecting said cardiac events in the first and second electrograms;

transmitting the first and second electrograms and at least one of first and second cardiac event detection marks with a corresponding one of the first and second electrograms to an external nonimplantable receiver;

receiving the first and second electrograms and the at least one of the first and second cardiac event detection markers; and displaying the at least one of the first and second cardiac event detection markers simultaneously with the corresponding one of the first and second electrograms.

19. A method as defined in claim 18 including the further steps of establishing first and second detection thresholds for the detection of the cardiac events in the first and second electrograms respectively, and displaying at least one of the first and second detection thresholds simultaneously with the corresponding one of the first and second electrograms and first and second cardiac event detection markers.

20. A method as defined in claim 19 including the further steps of transmitting data from the defibrillator indicative of the first and second detection thresholds and wherein the displaying step includes displaying the at least one of the first and second detection thresholds in accordance with said data.

21. A method as defined in claim 18 including the further steps of analyzing corresponding cardiac cycles of the first and second electrograms to determine if they satisfy a synchronization criteria, providing a synchronization marker whenever corresponding cardiac cycles of the first and second electrograms satisfy the synchronization criteria, transmitting the synchronization markers with the first and second electrograms, and displaying the synchronization markers simultaneously with the first and second electrograms and the at least one of the first and second cardiac event detection markers.

22. A method of verifying detection capability of an implantable defibrillator, the method including the steps of:

with the implantable defibrillator;

sensing electrical activity of the heart and generating an electrogram, establishing a threshold and with the threshold, detecting cardiac events in the electrogram, generating an event detection marker with each detection of a cardiac event, and transmitting the electrogram and the event detection markers to a nonimplantable external receiver, and with a nonimplantable receiver;

receiving the electrogram and the event detection markers, and simultaneously displaying the electrogram, the threshold, and the event detection markers.

23. A method as defined in claim 22 including the further steps of transmitting from the implantable defibrillator data indicative of the threshold and wherein the displaying step includes displaying the threshold in accordance with the transmitted data.

24. An implantable defibriltator for applying cardioverting electrical energy to a human heart, said defibrillator comprising:

first sensing means for sensing electrical activity of the heart and generating first electrogram data representing a first electrogram;

second sensing means for sensing electrical activity of the heart and generating second electrogram data representing a second electrogram;

cardioverting means responsive to at least one of the first and second sensing means for applying the cardioverting electrical energy to the heart; and transmitting means for transmitting the first electrogram data with the second electrogram data to a nonimplantable external receiver for simultaneous display of the first and second electrogram.

25. A defibrillator system for applying cardioverting electrical energy to a human heart, said system comprising:

an implantable defibrillator including first sensing means for sensing electrical activity of the heart and generating first electrogram data representing a first electrogram, second sensing means for sensing electrical activity of the heart and generating second electrogram data representing a second electrogram, cardioverting means responsive to at least one of the first and second sensing means for applying the cardioverting electrical energy to the heart, and transmitting means for transmitting the first electrogram data with the second electrogram data; and nonimplantable receiving means for receiving the first and second electrogram data and including display means responsive to the received first and second electrogram data for simultaneously displaying the first and second electrograms.

26. A defibrillator system for applying cardioverting electrical energy to a human heart, said system comprising:

an implantable defibrillator including first sensing means for sensing electrical activity of the heart and generating first electrogram data representing a first electrogram, second sensing means for sensing electrical activity of the heart and generating second electrogram data representing a second electrogram, cardioverting means responsive to at least one of the first and second sensing means for applying the cardioverting electrical energy to the heart, and transmitting means for transmitting the first electrogram data with the second electrogram data as said first and second sensing means generate the first and second electrogram data respectively; and nonimplantable receiving means for receiving the first and second electrogram data and including display means responsive to the first and second electrogram data for simultaneously displaying the first and second electrograms as said first and second sensing means generate the first and second electrogram data to provide a continuous running simultaneous display of said first and second electrograms.

* * * * *